(12) United States Patent
Yen et al.

(10) Patent No.: US 8,962,160 B2
(45) Date of Patent: Feb. 24, 2015

(54) MATERIAL FOR ORGANIC ELECTROLUMINESCENT DEVICE

(71) Applicant: Luminescence Technology Corporation, Hsin-Chu (TW)

(72) Inventors: Feng-Wen Yen, Hsin-Chu (TW); Cheng-Hao Chang, Hsin-Chu (TW)

(73) Assignee: Feng-Wen Yen, Taipei (TW)

( * ) Notice: Subject to any disclaimer, the term of this patent is extended or adjusted under 35 U.S.C. 154(b) by 294 days.

(21) Appl. No.: 13/726,640

(22) Filed: Dec. 26, 2012

(65) Prior Publication Data

US 2014/0175384 A1    Jun. 26, 2014

(51) Int. Cl.
*H01L 51/54* (2006.01)
*H01L 51/00* (2006.01)

(52) U.S. Cl.
CPC .......... *H01L 51/0058* (2013.01); *H01L 51/006* (2013.01); *Y10S 428/917* (2013.01)
USPC ........... 428/690; 428/917; 313/504; 313/505; 313/506; 257/40; 257/E51.05; 257/E51.026; 257/E51.032; 257/E51.044; 585/27

(58) Field of Classification Search
None
See application file for complete search history.

(56) References Cited

U.S. PATENT DOCUMENTS

| | | | |
|---|---|---|---|
| 5,935,721 A | 8/1999 | Shi et al. | |
| 7,691,492 B2 | 4/2010 | Yamada et al. | |
| 7,839,074 B2 | 11/2010 | Ikeda et al. | |
| 7,985,491 B2 | 7/2011 | Kubota et al. | |
| 2004/0076853 A1 | 4/2004 | Jarikov | |
| 2011/0073845 A1* | 3/2011 | Tseng et al. | 257/40 |

FOREIGN PATENT DOCUMENTS

| | | |
|---|---|---|
| WO | 2006130598 | 7/2006 |
| WO | 2012035962 | 3/2012 |

* cited by examiner

*Primary Examiner* — Gregory Clark

(57) ABSTRACT

The present invention discloses a novel material is represented by the following formula (A), the organic EL device employing the material as blue emitting layer can lower driving voltage, prolong half-lifetime and increase the efficiency.

formula(A)

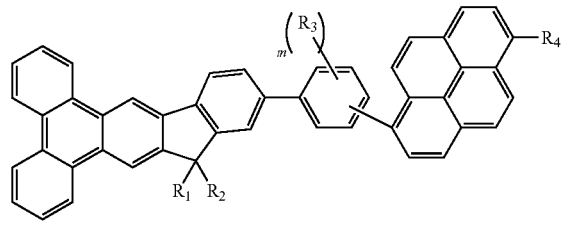

Wherein m represent an integer of 0 to 4, $R_1$ and $R_2$ are identical or different. $R_1$ and $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms. $R_3$ and $R_4$ are identical or different, $R_3$ and $R_4$ are independently selected from the group consisting of hydrogen atom, a halide, a substituted or unsubstituted arylamine, a substituted or unsubstituted alkyl group having 1 to 20 carbon atoms, a substituted or unsubstituted aryl group having 6 to 30 carbon atoms.

7 Claims, 1 Drawing Sheet

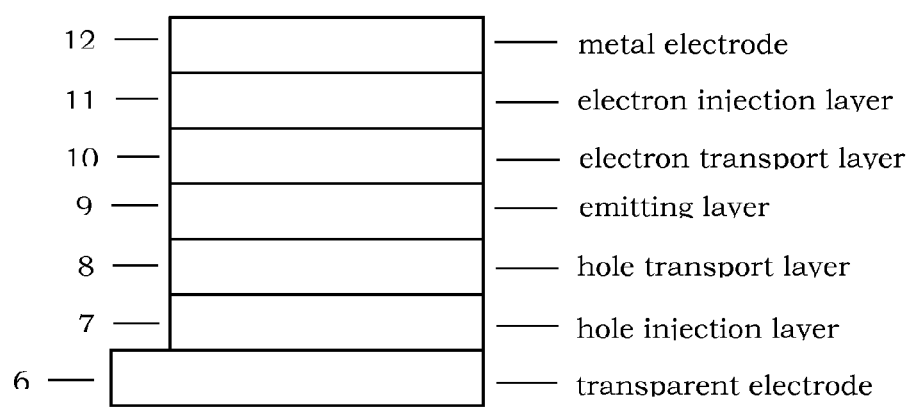

MATERIAL FOR ORGANIC ELECTROLUMINESCENT DEVICE

FIELD OF INVENTION

The present invention generally relates to a novel material and organic electroluminescent (herein referred to as organic EL) device using the material. More specifically, the present invention relates to the material having general formula (A), an organic EL device employing the material as fluorescent blue emitting material.

BACKGROUND OF THE INVENTION

Organic EL device has many advantages such as self-emitting, wider viewing angles, faster response speeds and highly luminescence. Their simpler fabrication and capable of giving clear display comparable with LCD, making organic EL device an industry display of choice. Organic EL device contain emissive materials which are arranged between a cathode and a anode, when a applied driving voltage is added, an electron and a hole were injected into the emissive layer and recombined to form an exciton. The exciton which results from an electron and a hole recombination have a singlet spin state or triplet spin state. Luminescence from a singlet spin state emits fluorescence and luminescence from triplet spin state emits phosphorescence.

Organic EL device are generally composed of functionally divided organic multi-layers, e.g., hole injection layer (HIL), hole transporting layer (HTL), emissive layer (EML), electron transporting layer (ETL) and electron injection layer (EIL) and so on. A emitting material have good charge carrier mobility and excellent operational durability can lower driving voltage and power consumption, increasing efficiency and half-lifetime of organic EL device.

For full-colored flat panel displays in AMOLED, the material used for the blue emitting layer are still unsatisfactory in half-lifetime and driving voltage. Many materials are used for fluorescent blue host in emitting layer. U.S. Pat. No. 5,935,721 used 9,10-di(naphtha-2-yl)anthrance (AND) as blue host in emitting layer. U.S. Pat. No. 7,691,492 used 1,1'-(9,9-dimethyl-9H-fluorine-2,7-diyl)dipyrene (DFDP) as host for blue emitting electroluminescence device. U.S. Pat. No. 7,985,491B2, U.S. Pat. No. 7,839,074B2 claimed anthracene derivatives as host for blue organic EL device. These compounds still have disadvantages for industrial practice use.

In the present invention, for the purpose to prolong the half-life time and lower driving voltage for fluorescent blue emitting organic EL device, we employ an indenotriphenylene skeleton link to a 6-position substituted 1-phenylpyrene to finish the material represented as general formula (A). The triphenylene skeleton show good thermal stability and charge carrier mobility for organic EL device. Triphenylene skeleton based derivative disclosed in U.S. Patent No. 20040076853, WO2006130598 and WO2012035962A1 are used for organic EL device are described. There are no prior arts demonstrate an indenotriphenylene skeleton link to a 6-position substituted 1-phenylpyrene compounds used as fluorescent blue host for organic EL device.

SUMMARY OF THE INVENTION

In accordance with the present invention, the material and their use as emitting material for organic EL device are provided. The material can overcome the drawbacks of the conventional material like as shorter half-life time, higher driving voltage and power consumption, especially for blue fluorescent emitting material in the present invention. For full-colored flat panel displays, the blue emitting material is still not satisfied for practice use for its shorter half-life time and higher driving voltage.

An object of the present invention is to provide the material which can be used as emitting material for organic EL device.

Another object of the present invention is to apply the material for fluorescent blue emitting material of organic EL device and improve the half-lifetime, lower driving voltage, lower power consumption.

The present invention has the economic advantages for industrial practice. Accordingly the present invention discloses the material which can be used for organic EL device is disclosed. The mentioned material are represented by the following formula (A):

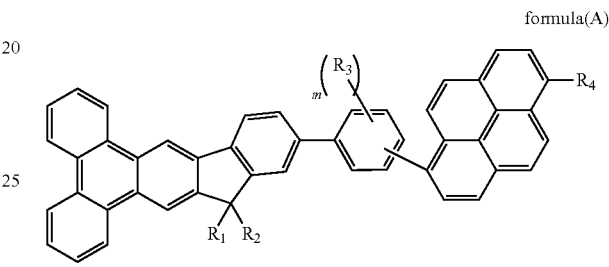

formula(A)

Wherein m represent an integer of 0 to 4, $R_1$ and $R_2$ are identical or different. $R_1$ and $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms. $R_3$ and $R_4$ are identical or different, $R_3$ and $R_4$ are independently selected from the group consisting of hydrogen atom, a halide, a substituted or unsubstituted arylamine, a substituted or unsubstituted alkyl group having 1 to 20 carbon atoms, a substituted or unsubstituted aryl group having 6 to 30 carbon atoms.

BRIEF DESCRIPTION OF THE DRAWINGS

FIG. 1 show one example of organic EL device in the present invention. 6 is transparent electrode, 12 is metal electrode, 7 is hole injection layer which is deposited onto 6, 8 is hole transporting layer which is deposited onto 7, 9 is fluorescent emitting layer which is deposited onto 8, 10 is electron transporting layer which is deposited onto 9, 11 is electron injection layer which is deposited onto 10.

DESCRIPTION OF THE PREFERRED EMBODIMENTS

What probed into the invention is the material and organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

DEFINITION

In a first embodiment of the present invention, the material which can be used as fluorescent blue emitting material of organic EL device are disclosed. The mentioned material are represented by the following formula (A):

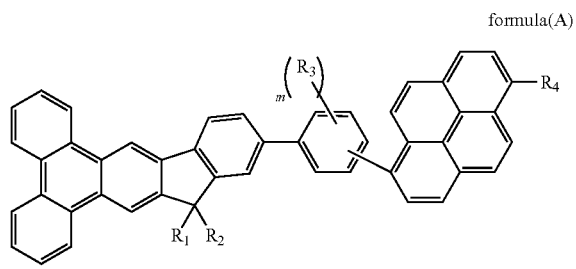

formula(A)

Wherein m represent an integer of 0 to 4, $R_1$ and $R_2$ are identical or different. $R_1$ and $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms. $R_3$ and $R_4$ are identical or different, $R_3$ and $R_4$ are independently selected from the group consisting of hydrogen atom, a halide, a substituted or unsubstituted arylamine, a substituted or unsubstituted alkyl group having 1 to 20 carbon atoms, a substituted or unsubstituted aryl group having 6 to 30 carbon atoms.

According to the formula (A), preferable $R_1$ and $R_2$ represented by the group like methyl group, ethyl group, propyl group, isopropyl group, butyl group, tert-butyl group, phenyl group, p-tolyl group, m-tolyl group, o-tolyl group. preferable $R_3$ and $R_4$ represented by the group like hydrogen, bromide, methyl group, ethyl group, propyl group, isopropyl group, butyl group, tert-butyl group, phenyl group, 1-biphenyl group, 2-biphenyl group, 3-biphenyl group, 1-naphthalene group, 2-naphthalene group, diphenylamine group, di-p-tolylamine group, di-1-naphthaleneamine group amine group, di-2-naphthaleneamine group, N-1-naphthalene 2-naphthaleneamine group.

In this embodiment, some materials are shown below:

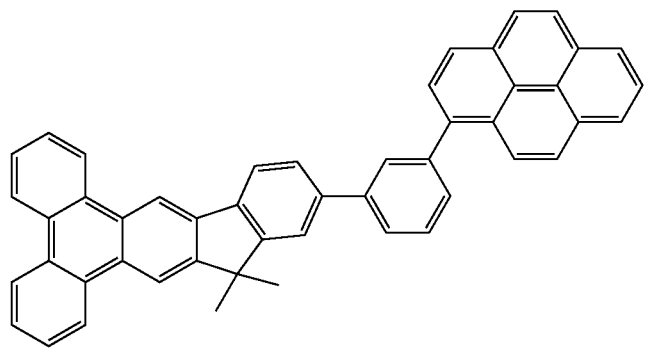

A-1

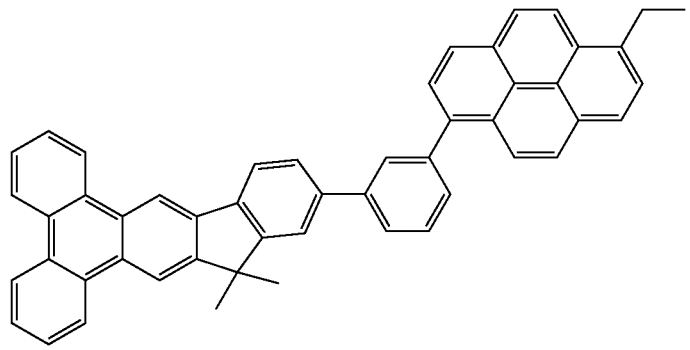

A-2

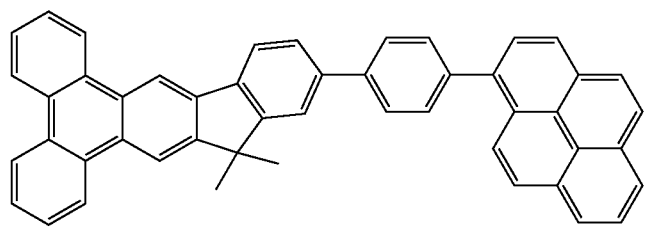

A-3

-continued
A-4
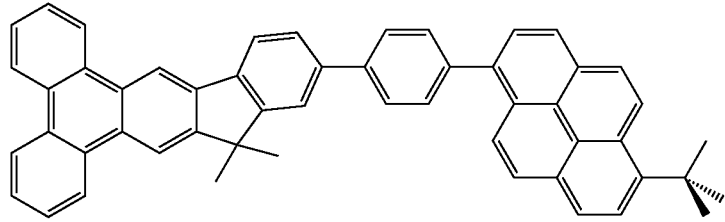
A-5
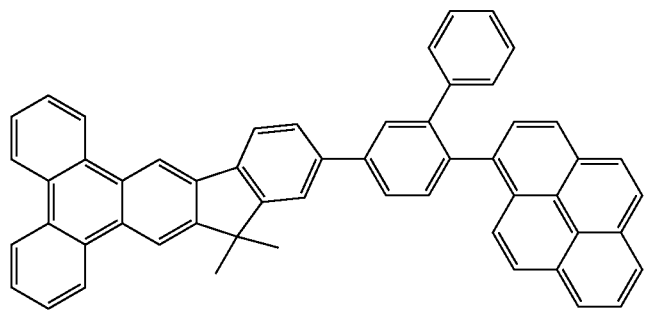
A-6
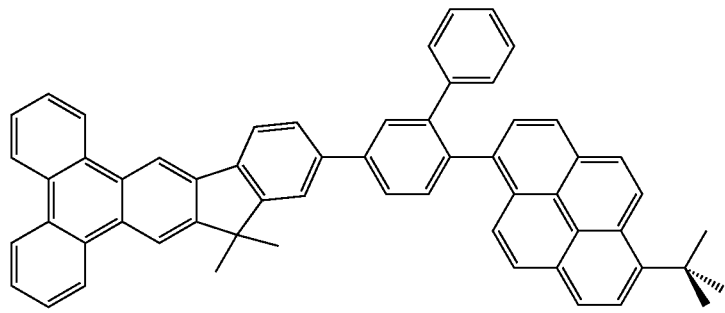
A-7
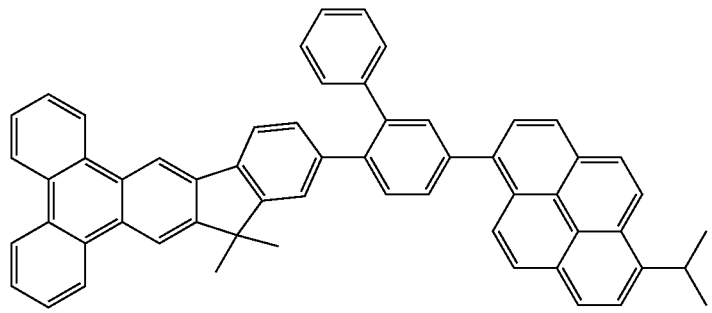
A-8
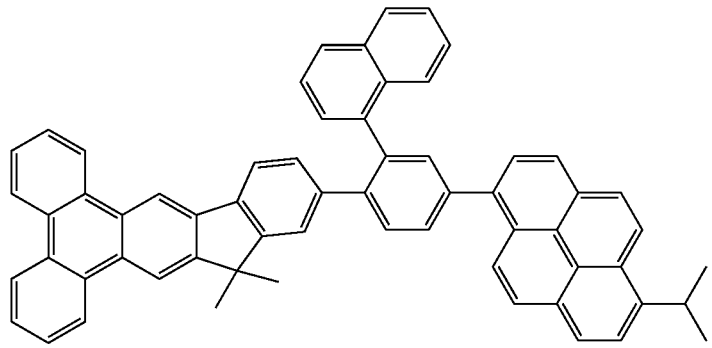

-continued
A-9
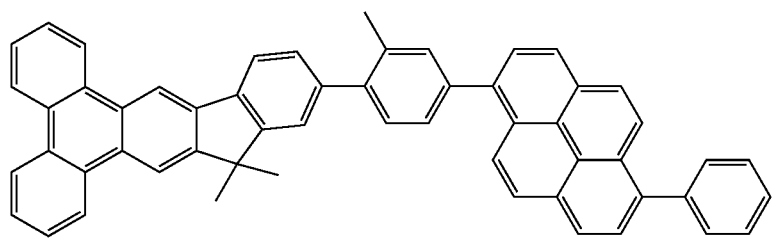
A-10
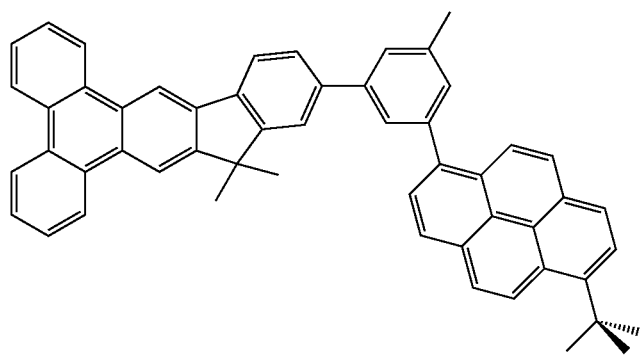
A-11
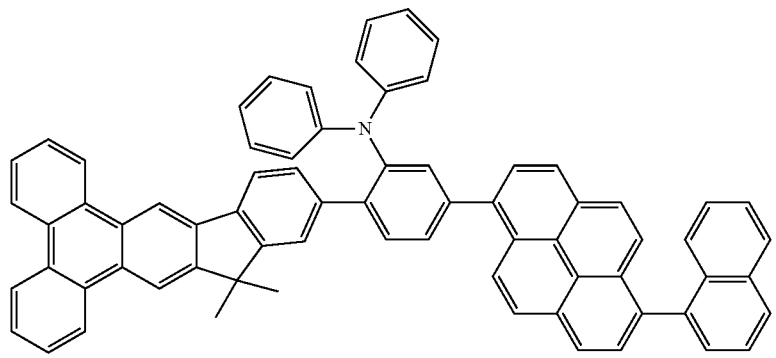
A-12
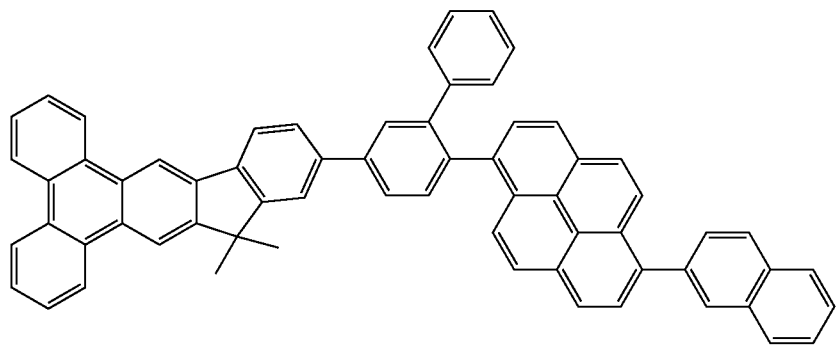
A-13
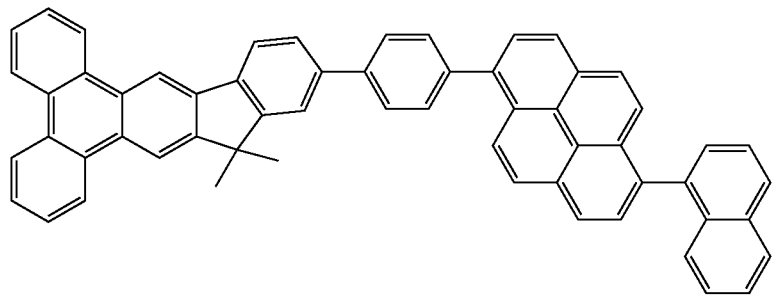

-continued
A-14
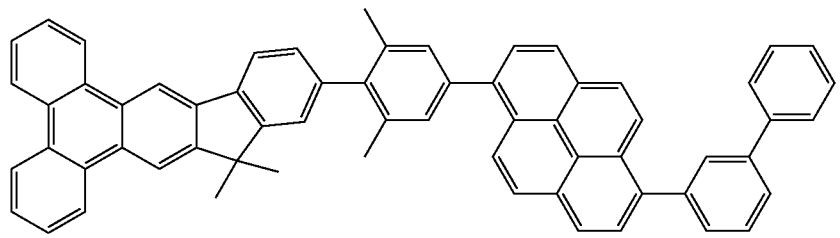
A-15
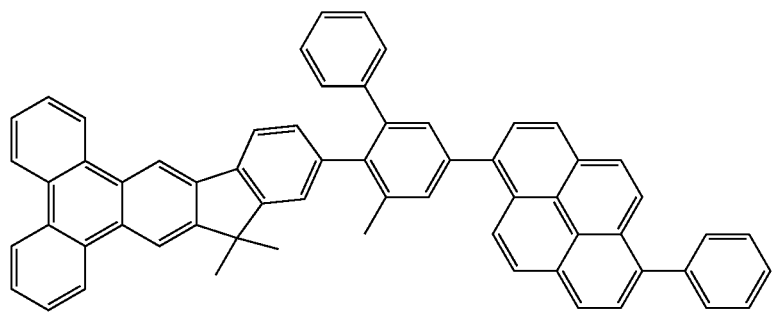
A-16
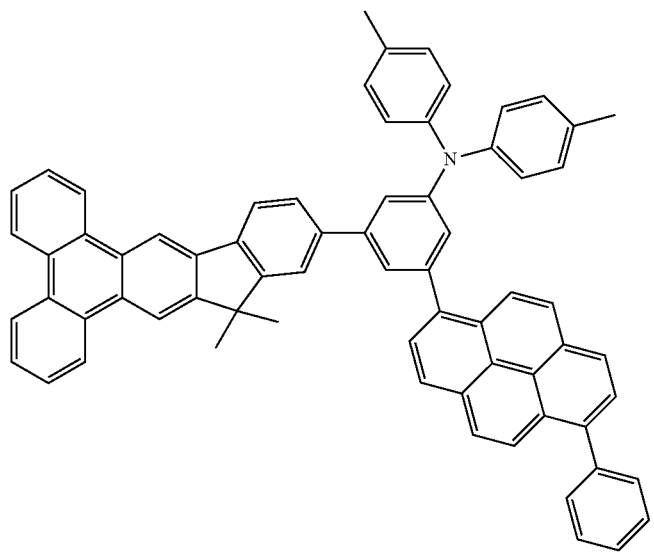
A-17
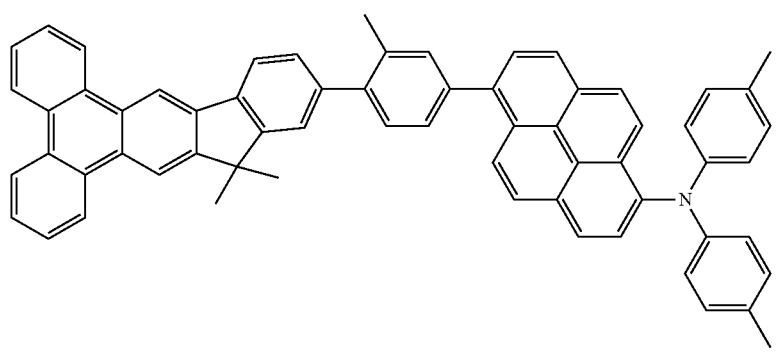

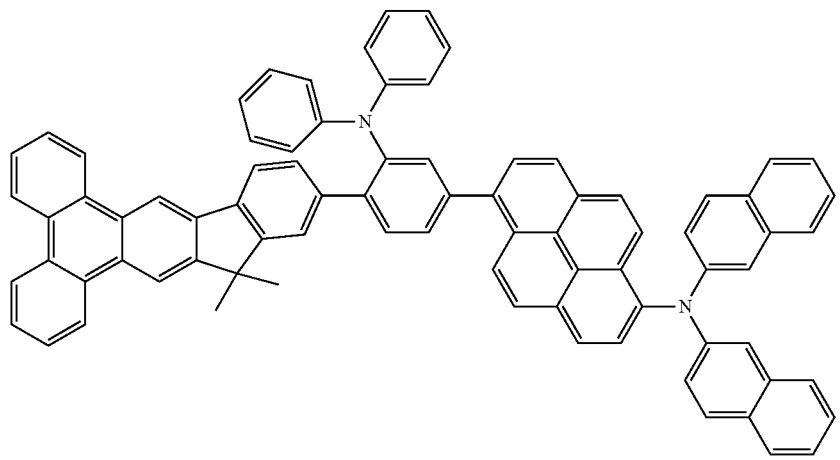
A-18
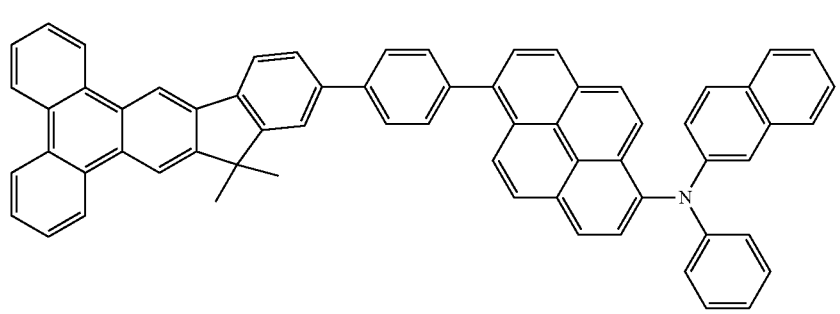
A-19
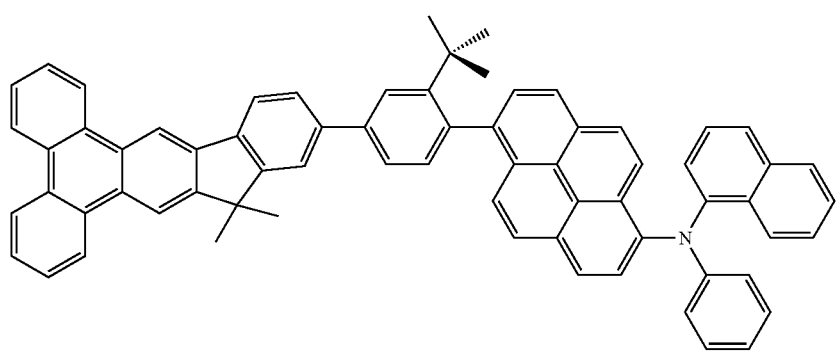
A-20

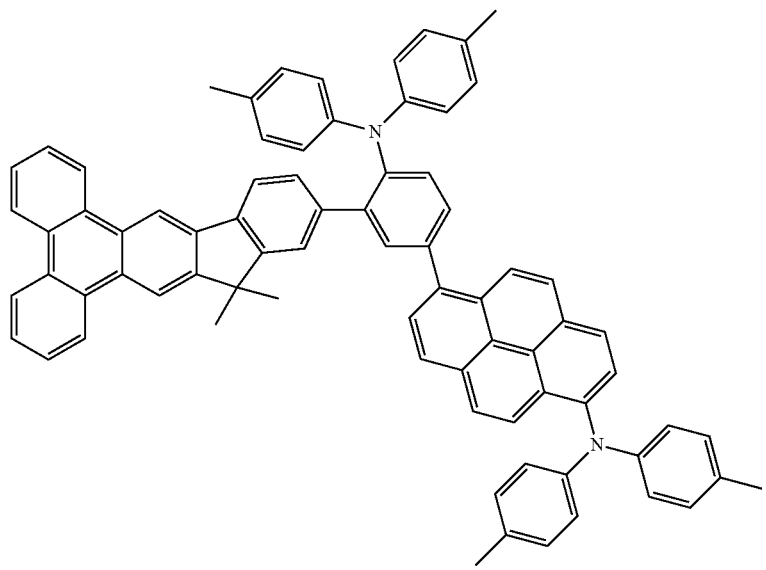

A-21

Detailed preparation for formula (A) could be clarified by exemplary embodiments, but the present invention is not limited to exemplary embodiments.

EXAMPLE 1

Synthesis of Compound A-1

Synthesis of 2-(biphenyl-2-yl)-7-bromo-9,9-dimethyl-9H-fluorene

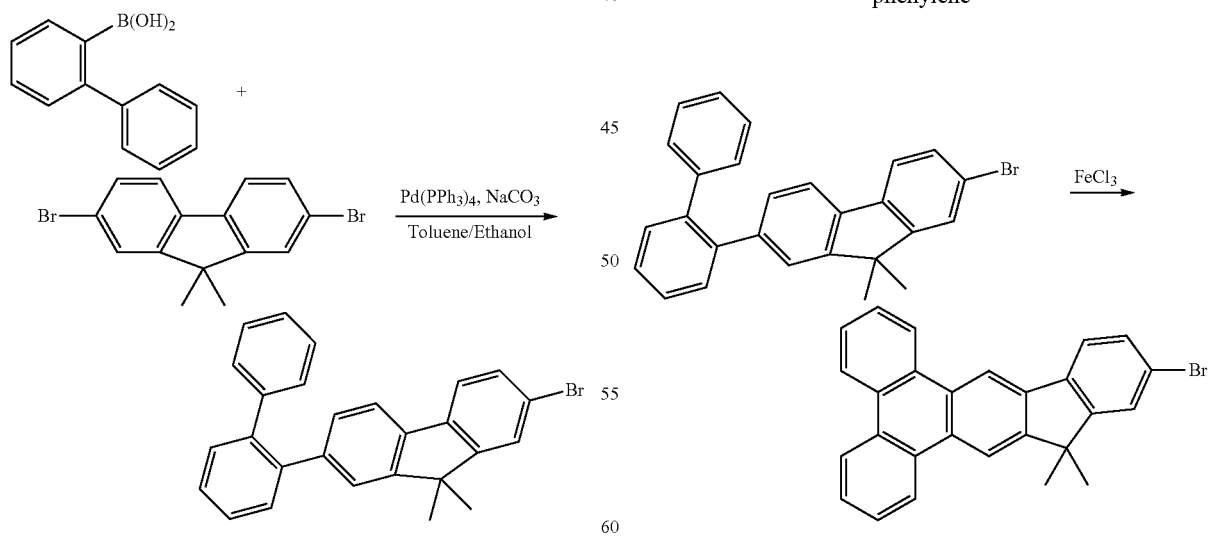

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of tetrakis(triphenylphosphine) palladium, 75 ml of 2M $Na_2CO_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product (26.8 g, 63.0 mmol, 63%) as a white solid. $^1$H NMR ($CDCl_3$, 400 MHz): chemical shift (ppm) 7.61 (d, J=7.8 Hz, 1H), 7.55~7.53 (m, 2H), 7.49~7.42 (m, 5H), 7.29 (d, J=8.0 Hz, 1H), 7.20~7.14 (m, 5H), 6.98 (s, 1H), 1.21 (s, 6H)

Synthesis of 12-bromo-10,10-dimethyl-10H-indeno[1,2-b]triphenylene

In a 3000 ml three-necked flask that had been degassed and filled with nitrogen, 26.8 mmol (60 mmol) of 2-(biphenyl-2-yl)-7-bromo-9,9-dimethyl-9H-fluorene was dissolved in anhydrous dichloromethane (1500 ml), 97.5 g (600 mmol) Iron (III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). ¹H NMR (CDCl₃, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[1,2-b]triphenylen-12-yl)-4,4,5,5-tetramethyl-1,3,2-dioxaborolane

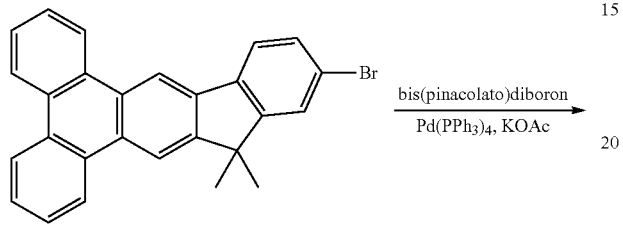

A mixture of 10.7 g (25.3 mmol) of 12-bromo-10,10-dimethyl-10H-indeno[1,2-b]triphenylene, 7.7 g (30.3 mmol) of bis(pinacolato)diboron, 0.3 g (0.26 mmol) of tetrakis(triphenylphosphine)palladium, 7.4 g (75.4 mmol) of potassium acetate, and 300 ml 1,4 dioxane was degassed and placed under nitrogen, and then heated at 90° C. for 16 h. After finishing the reaction, The mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (9.5 g, 20.2 mmol, 80%) as a light-yellow solid; ¹H NMR (CDCl₃, 400 MHz): chemical shift (ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

Synthesis of 1-(3-bromophenyl)pyrene

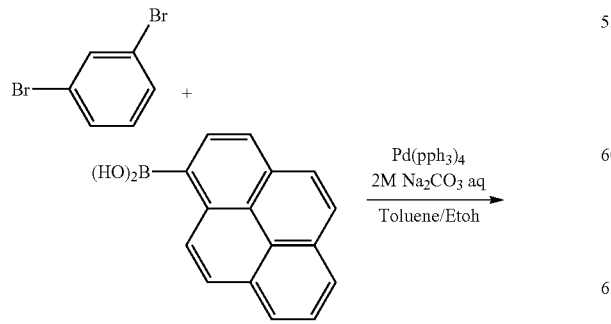

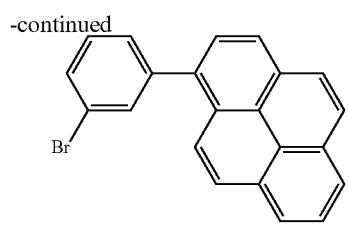

A mixture of 10 g (42.4 mmol) of 1,3-dibromobenzene, 10.43 g (42.4 mmol) of pyren-1-ylboronic acid, 0.5 g (0.424 mmol) of tetrakis(triphenylphosphine)palladium, 32 ml of 2M Na₂CO₃, 80 ml of EtOH and 160 ml toluene was degassed and placed under nitrogen, and then heated at 90° C. for 24 h. After finishing the reaction, The mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 10.9 g (72%) as a white solid.

Synthesis of 10,10-dimethyl-12-(3-(pyren-1-yl)phenyl)-10H-indeno[2,1-b]triphenylene

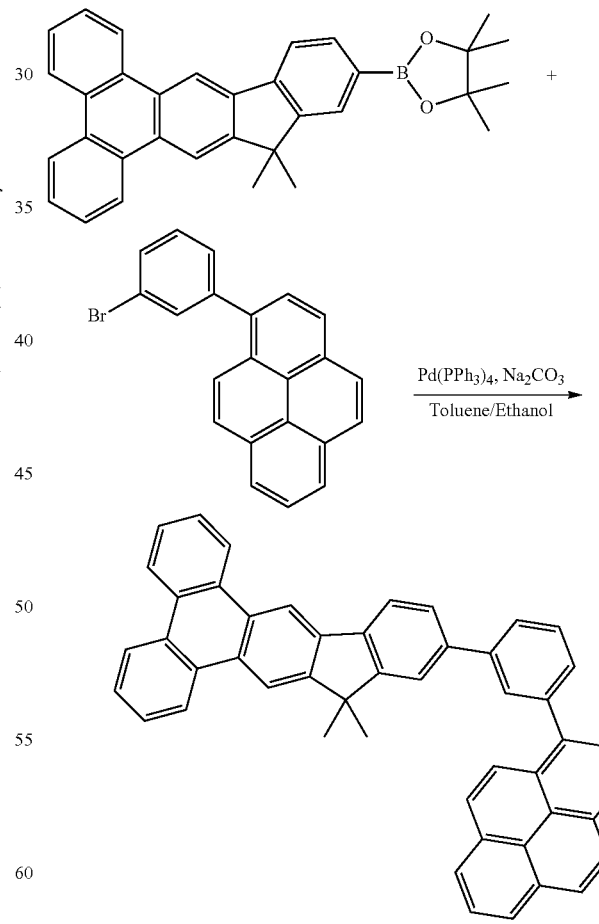

A mixture of 5 g (14 mmol) of 1-(3-bromophenyl)pyrene, 7.53 g (16 mmol) of 2-(10,10-dimethyl-10H-indeno[1,2-b]triphenylen-12-yl)-4,4,5,5-tetramethyl-1,3,2-dioxaborolane, 0.16 g (0.14 mmol) of tetrakis(triphenyl phosphine)palladium, 11 ml of 2M Na$_2$CO$_3$, 30 ml of EtOH and 65 ml toluene was degassed and placed under nitrogen, and then heated at 90° C. for 4 h. After finishing the reaction, the mixture was allowed to cool to room temperature. Than 500 ml MeOH was added, while stirring and the precipitated product was filtered off with suction to give 4.95 g (yield 57%) of yellow product which was recrystallized from toluene. MS(m/z, FAB$^+$): 620.1; $^1$H NMR (CDCl$_3$, 400 MHz): chemical shift (ppm) 9.05 (s, 1H), 8.46~8.41 (m, 2H), 8.40 (s, 1H), 8.06~7.84 (m, 9H), 7.74 (d, J=8.00 Hz, 1H), 7.69~7.59 (m, 4H), 7.54~7.39 (m, 5H), 7.31~7.16 (m, 3H), 1.82 (s, 6H).

EXAMPLE 2

Synthesis of Compound A-5

Synthesis of 1-(5-methoxybiphenyl-2-yl)pyrene

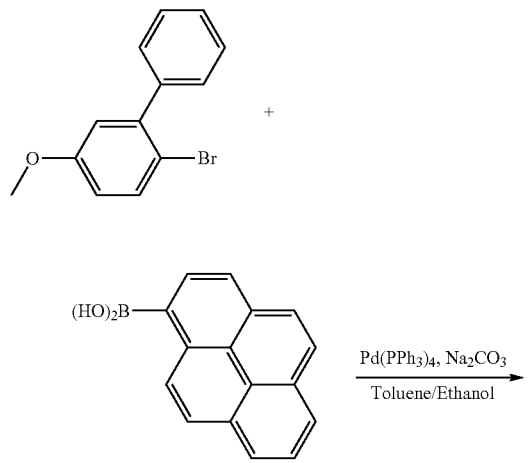

A mixture of 11.1 g (42.4 mmol) of 2-bromo-5-methoxybiphenyl, 10.43 g (42.4 mmol) of pyren-1-ylboronic acid, 0.5 g (0.424 mmol) of tetrakis(triphenylphosphine)palladium, 32 ml of 2M Na$_2$CO$_3$, 80 ml of EtOH and 160 ml toluene was degassed and placed under nitrogen, and then heated at 90° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 12.4 g (76%) as a white solid.

Synthesis of 6-(pyren-1-yl)biphenyl-3-ol

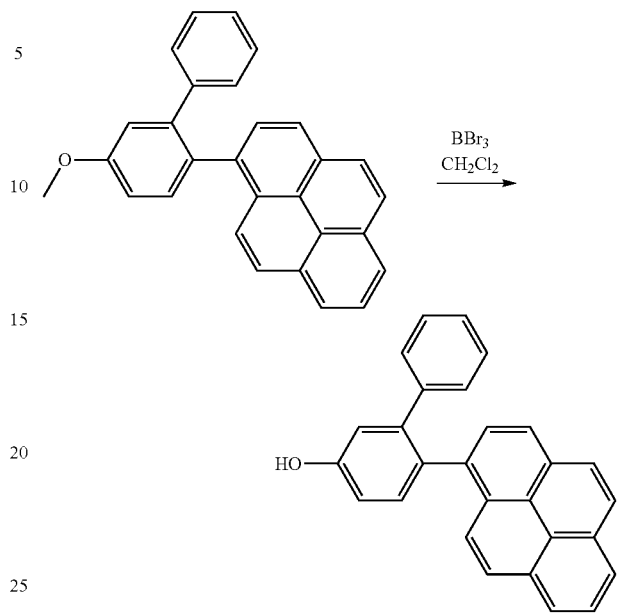

In a 1000 ml three-necked flask that had been degassed and filled with nitrogen, 12.4 g (32.2 mmol) of 1-(5-methoxybiphenyl-2-yl)pyrene was dissolved in anhydrous dichloromethane (200 ml), the solution was cooled to −78° C., and 24.2 g (96.6 mmol) boron tribromide was added slowly. The solution was warmed to room temperature and stirred overnight. 200 g Ice was carefully added to quench unreacted boron tribromide. The organic layer was extracted with dichloromethane and water, dried with anhydrous magnesium sulfate, the solvent was removed to give product 10.8 g (91%).

Synthesis of 6-(pyren-1-yl)biphenyl-3-yl trifluoromethanesulfonate

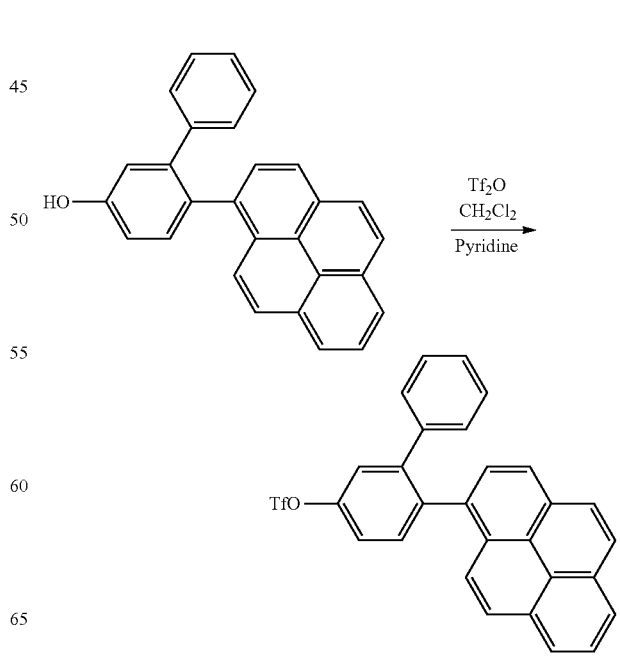

In a 1000 ml three-necked flask that had been degassed and filled with nitrogen, 10.8 g (29.1 mmol) of 6-(pyren-1-yl)biphenyl-3-ol and 4.66 g (58.2 mmol) of anhydrous pyridine was dissolved in anhydrous dichloromethane (500 ml), the solution was cooled to 0~5° C., and 16.5 g (58.2 mmol) trifluoromethanesulfonic anhydride was added slowly. The solution was warmed to room temperature and stirred overnight. The organic layer was extracted with dichloromethane and water, dried with anhydrous magnesium sulfate, the solvent was removed and the residue was purified by column chromatography on silica (hexane-dichloromethane) to give product 9.8 g (67%).

Synthesis of 10,10-dimethyl-12-(6-(pyren-1-yl)biphenyl-3-yl)-10H-indeno[2,1-b]triphenylene

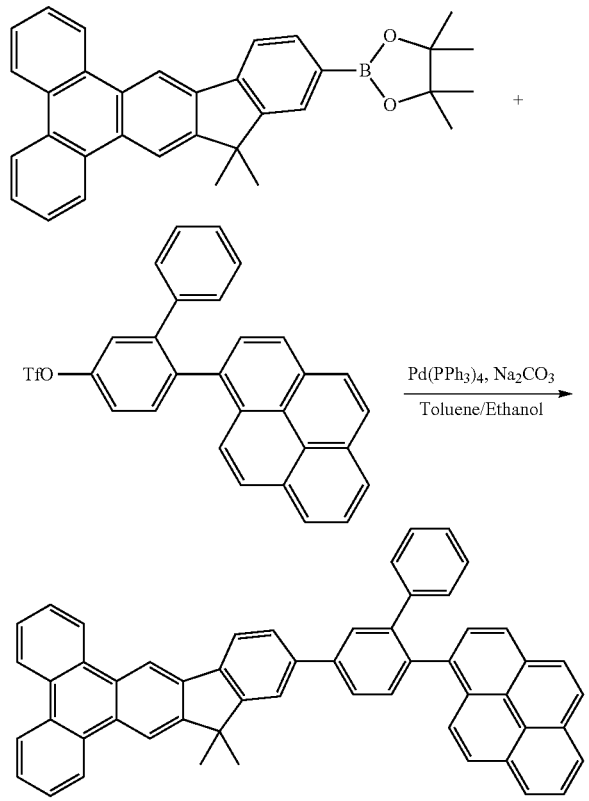

A mixture of 7 g (14 mmol) of 6-(pyren-1-yl)biphenyl-3-yltrifluoro methanesulfonate, 7.53 g (16 mmol) of 2-(10,10-dimethyl-10H-indeno [1,2-b]triphenylen-12-yl)-4,4,5,5-tetramethyl-1,3,2-dioxaborolane, 0.16 g (0.14 mmol) of tetrakis (triphenylphosphine)palladium, 11 ml of 2M Na$_2$CO$_3$, 30 ml of EtOH and 65 ml toluene was degassed and placed under nitrogen, and then heated at 90° C. for 4 h. After finishing the reaction, the mixture was allowed to cool to room temperature. Than 500 ml MeOH was added, while stirring and the precipitated product was filtered off with suction to give 4.8 g (yield 49%) of yellow product which was recrystallized from toluene. MS(m/z, FAB$^+$): 696.4; $^1$H NMR (CDCl$_3$, 400 MHz): chemical shift (ppm) 9.65 (s, 1H), 9.07 (s, 1H), 8.76~8.71 (m, 3H), 8.24~7.95 (m, 9H), 7.81~7.42 (m, 13H), 7.35 (d, J=8.00 Hz, 1H), 7.04 (d, J=8.00 Hz, 1H), 6.54 (d, J=8.00 Hz, 1H), 1.81 (s, 6H).

EXAMPLE 3

Synthesis of Compound A-13

Synthesis of 1-bromo-6-(naphthalen-1-yl)pyrene

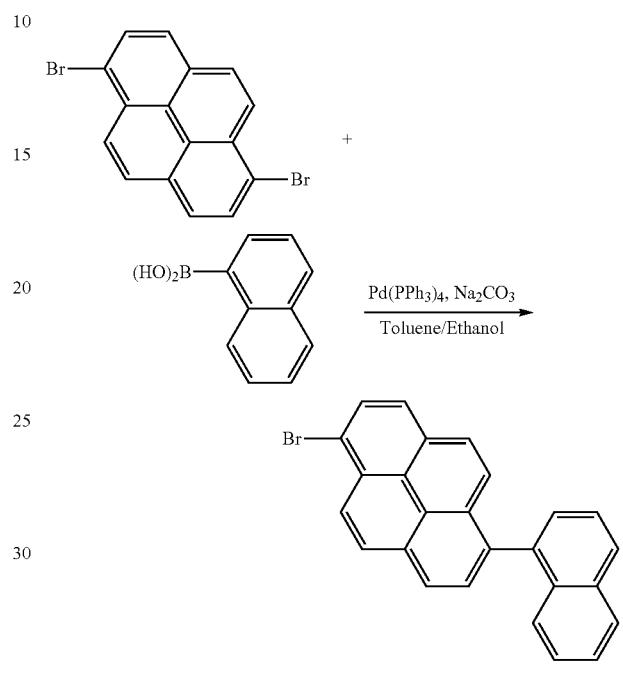

A mixture of 18 g (50 mmol) of 1,6-dibromopyrene, 8.6 g (50 mmol) of naphthalen-1-ylboronic acid, 0.6 g (0.5 mmol) of tetrakis(triphenylphosphine) palladium, 38 ml of 2M Na$_2$CO$_3$, 100 ml of EtOH and 200 ml toluene was degassed and placed under nitrogen, and then heated at 90° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 8 g (40%) as a white solid.

Synthesis of 12-(4-bromophenyl)-10,10-dimethyl-10H-indeno[2,1-b]triphenylene

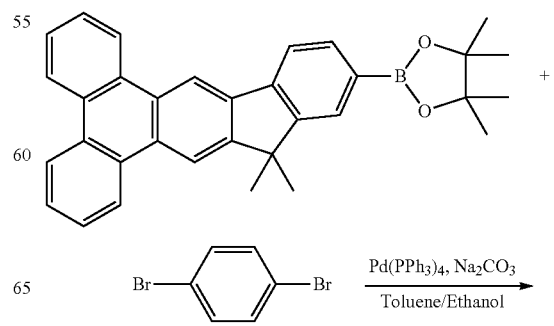

-continued

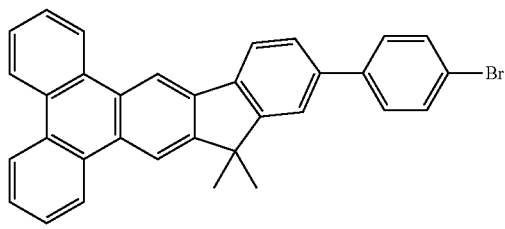

A mixture of 6.6 g (28 mmol) of 1,4-dibromobenzene, 15.1 g (32 mmol) of 2-(10,10-dimethyl-10H-indeno[1,2-b]triphenylen-12-yl)-4,4,5,5-tetra methyl-1,3,2-dioxaborolane, 0.32 g (0.28 mmol) of tetrakis(triphenylphosphine) palladium, 22 ml of 2M $Na_2CO_3$, 60 ml of EtOH and 130 ml toluene was degassed and placed under nitrogen and then heated at 90° C. for 12 h. After finishing the reaction, the mixture was allowed to cool to room temperature. Than 500 ml MeOH was added, while stirring and the precipitated product was filtered off with suction and the residue was purified by column chromatography on silica (hexane-dichloromethane) to give product 7.4 g (53%) as a white solid.

Synthesis of 2-(4-(10,10-dimethyl-10H-indeno[2,1-b]triphenylen-12-yl)phenyl)-4,4,5,5-tetramethyl-1,3,2-dioxaborolane

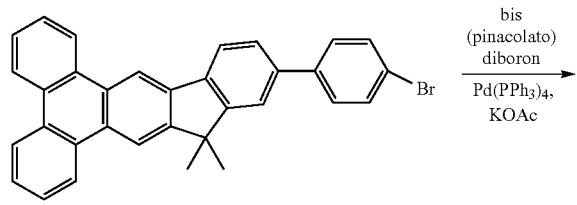

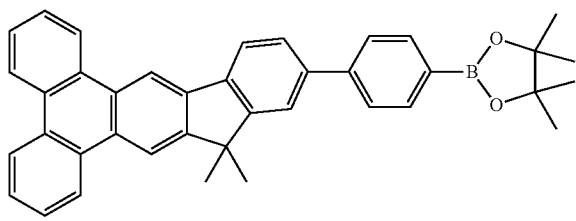

A mixture of 7.4 g (14.8 mmol) 12-(4-bromophenyl)-10,10-dimethyl-10H-indeno[2,1-b]triphenylene, 4.9 g (19.3 mmol) of bis(pinacolato)diboron, 0.17 g (0.148 mmol) of tetrakis(triphenylphosphine)palladium, 2.9 g (29.6 mmol) of potassium acetate, and 50 ml 1,4 dioxane was degassed and placed under nitrogen, and then heated at 90° C. for 24 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (5.9 g, 73%) as a white solid.

Synthesis of 10,10-dimethyl-12-(4-(6-(naphthalene-1-yl)pyren-1-yl)phenyl)-10H-indeno[2,1-b]triphenylene

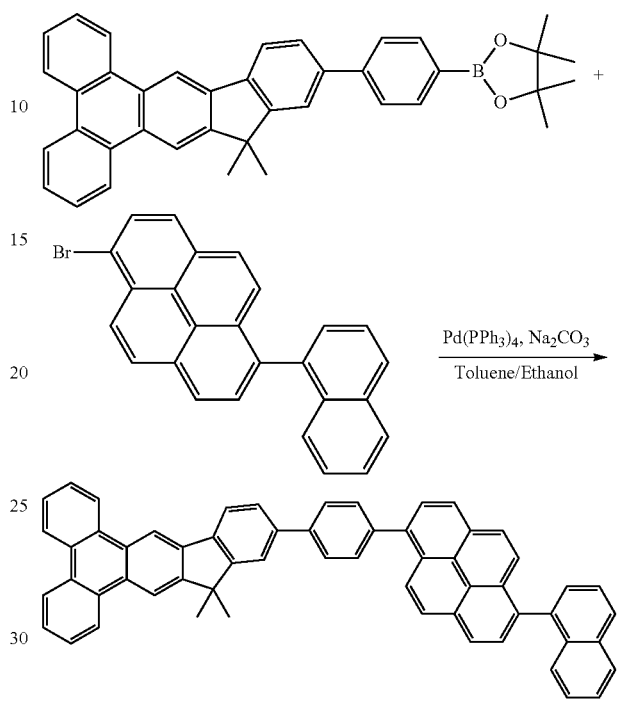

A mixture of 5.7 g (14 mmol) of 1-bromo-6-(naphthalen-1-yl)pyrene, 8.7 g (16 mmol) of 2-(4-(10,10-dimethyl-10H-indeno[2,1-b]triphenylen-12-yl) phenyl)-4,4,5,5-tetramethyl-1,3,2-dioxaborolane, 0.16 g (0.14 mmol) of tetrakis (triphenylphosphine)palladium, 11 ml of 2M $Na_2CO_3$, 30 ml of EtOH and 65 ml toluene was degassed and placed under nitrogen, and then heated at 90° C. for 4 h. After finishing the reaction, the mixture was allowed to cool to room temperature. Than 500 ml MeOH was added, while stirring and the precipitated product was filtered off with suction to give 4.8 g (yield 49%) of yellow product which was recrystallized from toluene. MS(m/z, $FAB^+$): 746.4; $^1H$ NMR ($CDCl_3$, 400 MHz): chemical shift (ppm) 9.07 (s, 1H), 8.74~8.69 (m, 3H), 8.17~8.06 (m, 6H), 7.87~7.53 (m, 15H), 7.48 (d, J=8.00 Hz, 1H), 7.42~7.38 (m, 1H), 7.30~7.25 (m, 4H), 7.13 (d, J=8.00 Hz, 1H), 1.84 (s, 6H).

EXAMPLE 4

Synthesis of Compound A-19

Synthesis of 6-bromo-N-(naphthalen-2-yl)-N-phenylpyren-1-amine

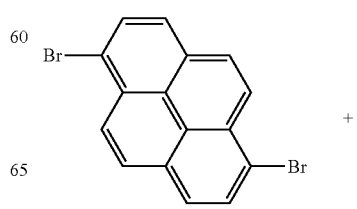

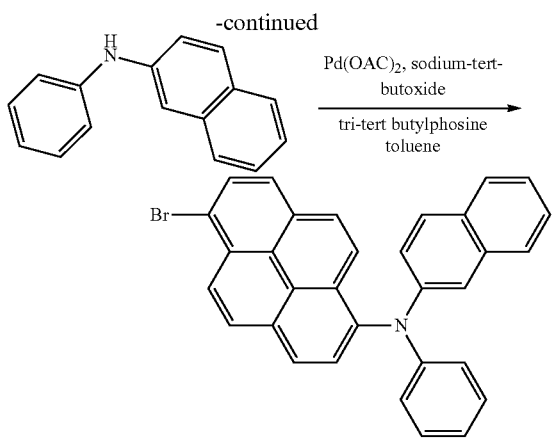

A mixture of 18 g (50 mmol) of 1,6-dibromopyrene, 11 g (50 mmol) of N-phenylnaphthalen-2-amine, 0.16 g (0.7 mmol) of Pd(OAC)$_2$, 0.5 g (1.4 mmole) of tri-tert-butylphosine, 6 g (75 mmol) sodium tert-butoxide was stirred in 200 ml dry toluene, the reaction mixture was then heat to 100° C. for about overnight under nitrogen. The solution was filtered. The toluene solution was removed under reduced pressure from the filtrate. The residue was extracted three times with dichloromethane and water, dried with MgSO$_4$ and filtered, and the dichloromethane was removed under reduced pressure. The product was purified by column chromatography to get 9.2 g of product (yield 37%).

Synthesis of 6-(4-(10,10-dimethyl-10H-indeno[2,1-b]triphenylen-12-yl)phenyl)-N-(naphthalen-2-yl)-N-phenylpyren-1-amine

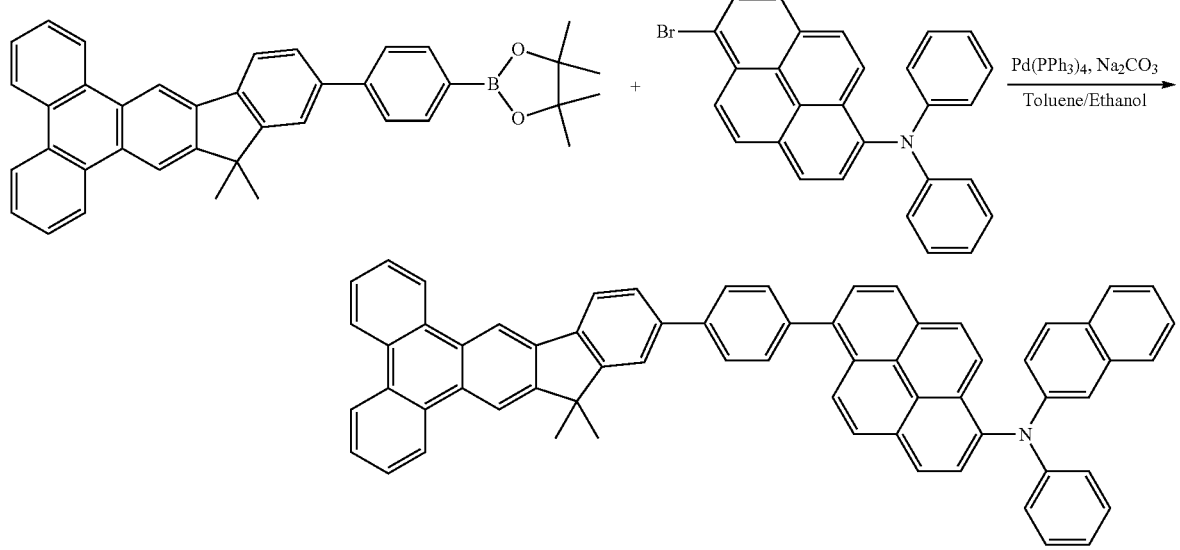

A mixture of 7 g (14 mmol) of 6-bromo-N-(naphthalen-2-yl)-N-phenylpyren-1-amine, 8.7 g (16 mmol) of 2-(4-(10,10-dimethyl-10H-indeno[2,1-b]triphenylen-12-yl)phenyl)-4,4,5,5-tetramethyl-1,3,2-dioxaborolane, 0.2 g (0.17 mmol) of tetrakis(triphenylphosphine)palladium, 11 ml of 2M Na$_2$CO$_3$, 30 ml of EtOH and 100 ml toluene was degassed and placed under nitrogen, and then heated at 90° C. for 24 h. After finishing the reaction, the mixture was allowed to cool to room temperature. Than 500 ml MeOH was added, while stirring and the precipitated product was filtered off with suction. To give 4.8 g (yield 49%) of yellow product which was recrystallized from toluene. MS(m/z, FAB$^+$): 837.5; NMR (CDCl$_3$, 400 MHz): chemical shift (ppm) 9.07 (s, 1H), 8.73~8.66 (m, 3H), 8.27~7.66 (m, 21H), 7.50~7.42 (m, 4H), 7.37 (d, J=8.00 Hz, 1H), 7.26~7.01 (m, 4H), 6.96~6.89 (m, 2H), 6.71 (d, J=8.00 Hz, 1H), 1.82 (s, 6H).

GENERAL METHOD OF PRODUCING ORGANIC EL DEVICE

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a guest material. This is achieved by co-vaporization from two or more sources.

Dipyrazino[2,3-f:2',3'-h]quinoxaline-2,3,6,7,10,11-hexacarbonitrile (HAT-CN) is used as hole injection layer in this organic EL device. N,N-Bis(naphthalene-1-yl)-N,N'-bis(phenyl)-benzidine (NPB) is most widely used as the hole transporting layer and 2,9-bis(naphthalene-2-yl)-4,7-diphenyl-1,10-phenanthroline (NBphen) is used as electron transporting material in organic EL device for its high thermal stability and long life-time than BPhen/BCP. 9,10-di(naphtha-2-yl)anthrance (AND, U.S. Pat. No. 5,935,721), 1,1'-(9,9-dimethyl-9H-fluorene-2,7-diyl)dipyrene (DFDP, U.S. Pat. No. 7,691,492) and 9-(4-(naphthalen-1-yl)phenyl)-10-

(naphthalen-2-yl) anthracene (H1, U.S. Pat. No. 7,839,074) are used as emitting host for comparative example, and (E)-6-(4-(diphenylamino)styryl)-N,N-diphenyl naphthalen-2-amine (D1) is used as guest. The above organic EL materials for producing standard organic EL device in this invention shown its chemical structure as following:

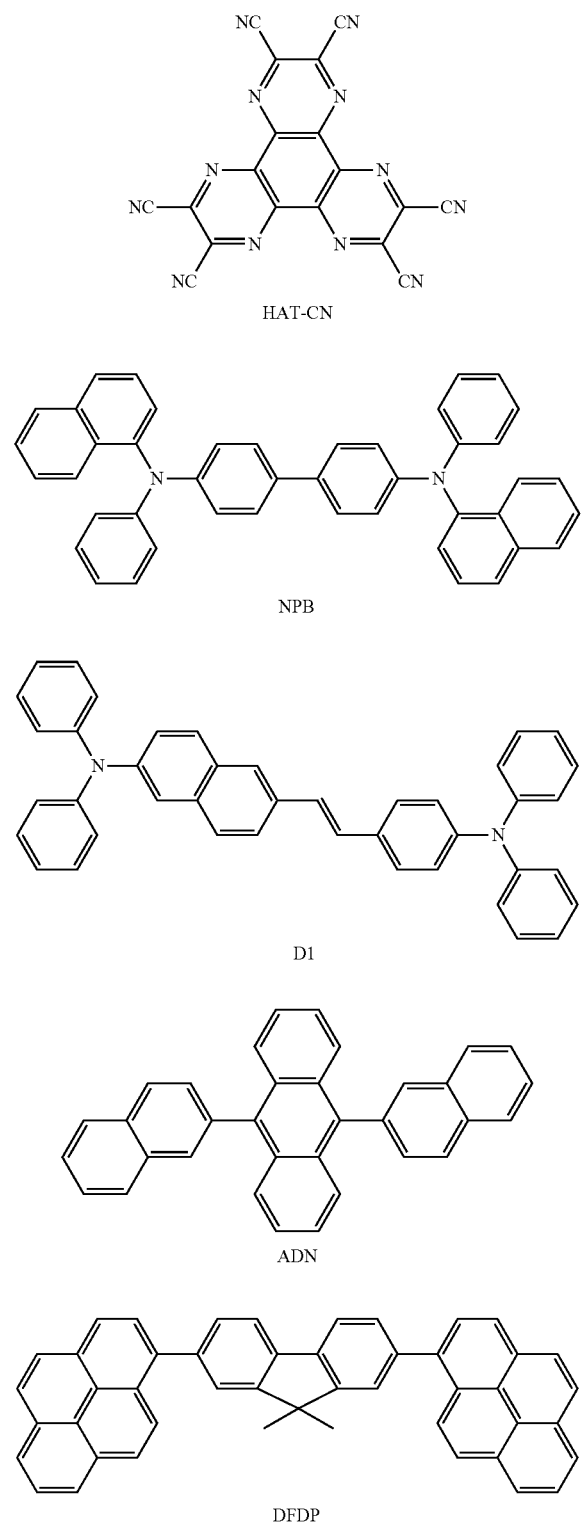

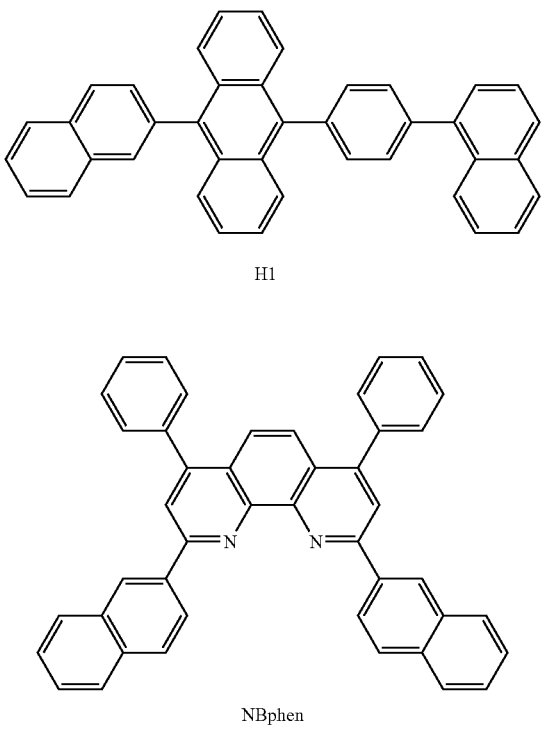

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 9

Using a procedure analogous to the above mentioned general method, fluorescent blue-emitting organic EL device having the following device structure were produced (See FIG. 1): ITO/HAT-CN (20 nm)/NPB (60 nm)/fluorescent blue host doped 5% DPASN (35 nm)/NPhen (30 nm)/LiF (0.5 nm)/Al (160 nm). The I-V-B and half-life time of fluorescent blue-emitting OLED device testing report as Table 1, The half-life time is defined that the initial luminance of 1000 $cd/m^2$ has dropped to half.

TABLE 1

| Fluorescent blue host | Voltage (V) | Luminance (cd/m$^2$) | Yield (cd/A) | CIE(y) | Half-life time (hour) Initial luminance = 1000(cd/m$^2$) |
|---|---|---|---|---|---|
| Compound A1 | 4.8 | 1000 | 5.8 | 0.172 | 560 |
| Compound A3 | 5.0 | 1000 | 5.6 | 0.178 | 580 |
| Compound A5 | 4.5 | 1000 | 5.5 | 0.180 | 520 |
| Compound A13 | 4.6 | 1000 | 6.1 | 0.185 | 600 |
| ADN | 8.9 | 1000 | 1.3 | 0.132 | 120 |
| DFDP | 7.8 | 1000 | 2.8 | 0.183 | 200 |
| H1 | 5.5 | 1000 | 6.5 | 0.162 | 430 |

In the above preferred embodiments, we show that the material formula (A) used as fluorescent blue host than comparable example AND,DFDP and H1 with higher half-life time and practical operation durability. Under the same Luminance (cd/m$^2$), lower driving voltage than comparable example AND,DFDP and H1 has also been achieved at 1000 cd/m$^2$ using the mentioned material formula (A) for blue-emitting organic EL devices. The efficiency of all present invention examples also show over 5.5 cd/A and better than comparable example AND and DFDP. The present invention formula (A) can be used as fluorescent blue host.

To sum up, the present invention discloses a material which can be used for organic EL device is disclosed. The mentioned material are represented by the following formula (A).

Formula(A)

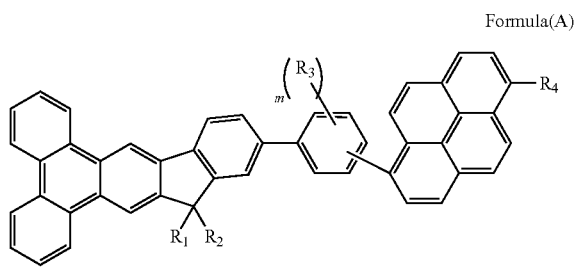

Wherein m represent an integer of 0 to 4, $R_1$ and $R_2$ are identical or different. $R_1$ and $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms. $R_3$ and $R_4$ are identical or different, $R_3$ and $R_4$ are independently selected from the group consisting of hydrogen atom, halide, a substituted or unsubstituted arylamine, a substituted or unsubstituted alkyl group having 1 to 20 carbon atoms, a substituted or unsubstituted aryl group having 6 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A organic EL material with a general formula(A) as following:

formula(A)

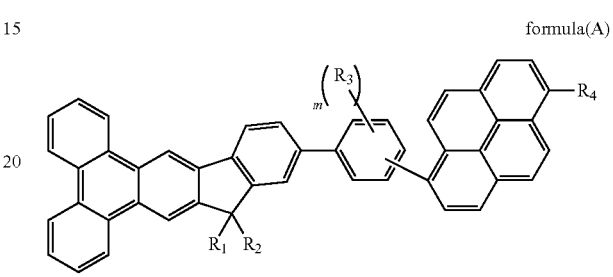

Wherein m represent an integer of 0 to 4, $R_1$ and $R_2$ are identical or different, $R_1$ and $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, $R_3$ and $R_4$ are identical or different, $R_3$ and $R_4$ are independently selected from the group consisting of hydrogen atom, a halide, a substituted or unsubstituted arylamine, a substituted or unsubstituted alkyl group having 1 to 20 carbon atoms, a substituted or unsubstituted aryl group having 6 to 30 carbon atoms.

2. According to claim 1, wherein $R_1$ and $R_2$ represented methyl group, ethyl group, propyl group, isopropyl group, butyl group, tert-butyl group, phenyl group, p-tolyl group, m-tolyl group, o-tolyl group.

3. According to claim 1, wherein $R_3$ and $R_4$ represented hydrogen, bromide, methyl group, ethyl group, propyl group, isopropyl group, butyl group, tert-butyl group, phenyl group, 1-biphenyl group, 2-biphenyl group, 3-biphenyl group, 1-naphthalene group, 2-naphthalene group, diphenylamine group, di-p-tolylamine group, di-1-naphthaleneamine group, di-2-naphthaleneamine group, N-1-naphthalene 2-naphthaleneamine group.

4. A organic EL device comprising a pair of electrodes consisting of a cathode and an anode and between the pairs of electrodes comprising a layer of material with a general formula(A) as following:

formula(A)

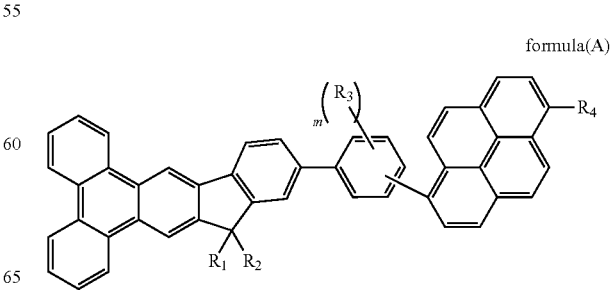

Wherein m represent an integer of 0 to 4, $R_1$ and $R_2$ are identical or different, $R_1$ and $R_2$ are independently selected from the group consisting of a hydrogen atom, alkyl group having 1 to 20 carbon atoms, a substituted or unsubstituted aryl group having 6 to 30 carbon atoms, a substituted or unsubstituted aralkyl group having 6 to 30 carbon atoms, $R_3$ and $R_4$ are identical or different, $R_3$ and $R_4$ are independently selected from the group consisting of hydrogen atom, a halide, a substituted or unsubstituted arylamine, a substituted or unsubstituted alkyl group having 1 to 20 carbon atoms, a substituted or unsubstituted aryl group having 6 to 30 carbon atoms.

5. According to claim 4, wherein the material is selected from the group consist of:

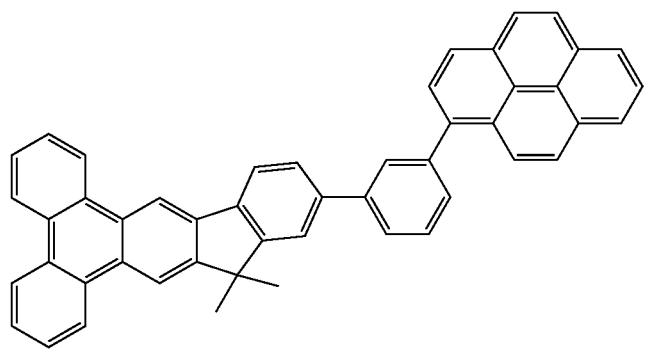

A-1

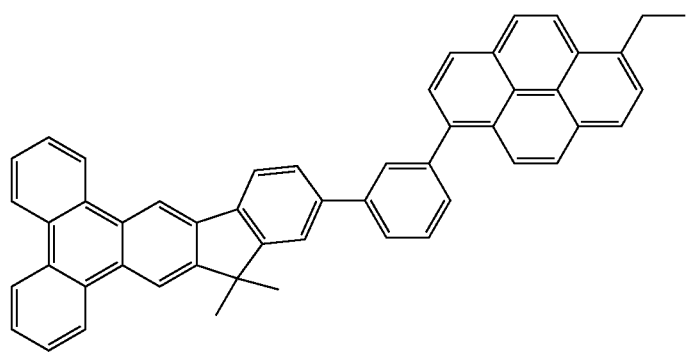

A-2

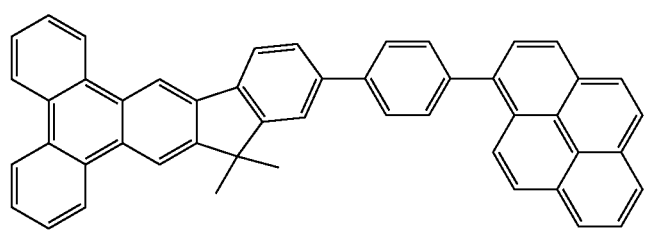

A-3

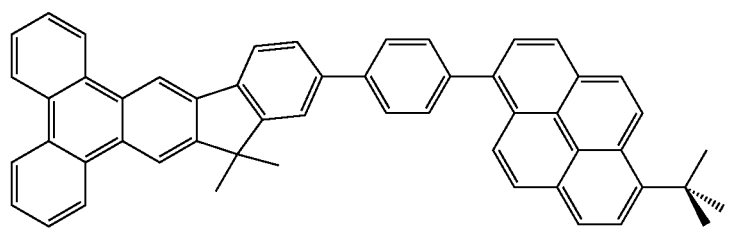

A-4

A-5
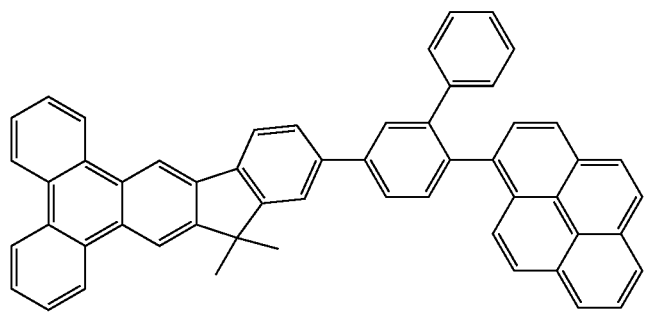
A-6
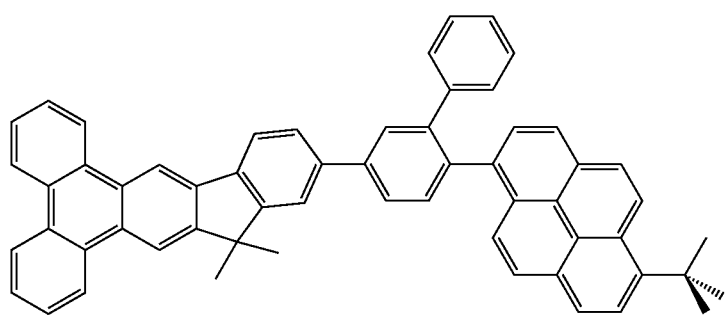
A-7
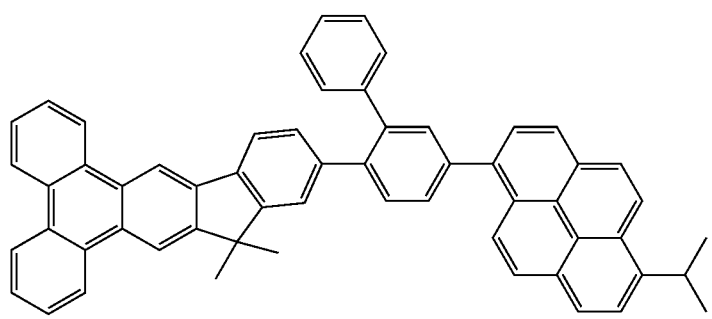
A-8
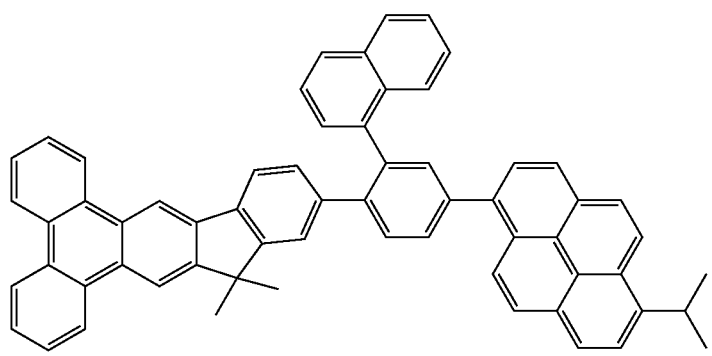
A-9
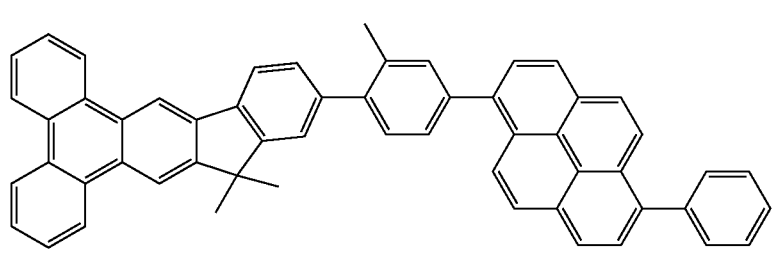

A-10
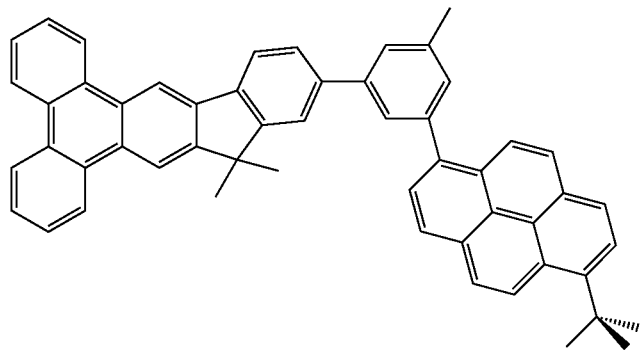
A-11
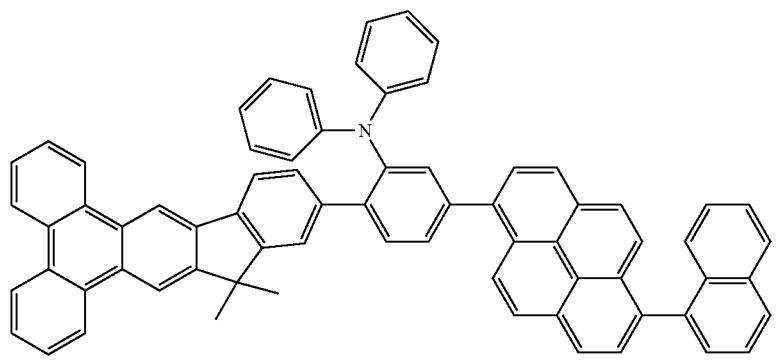
A-12
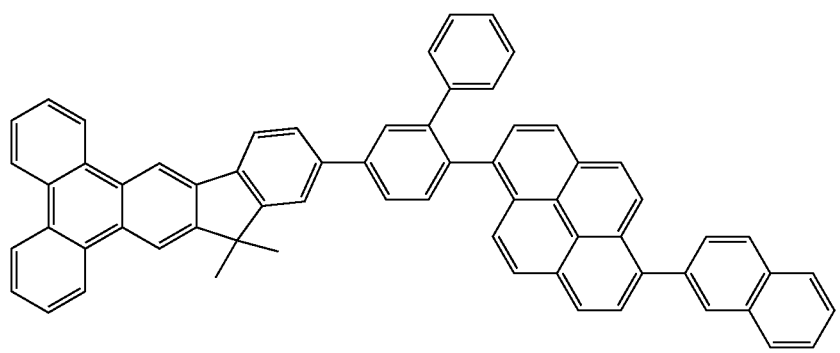
A-13
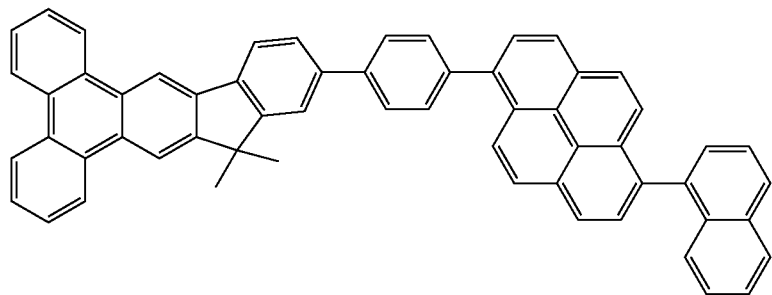
A-14
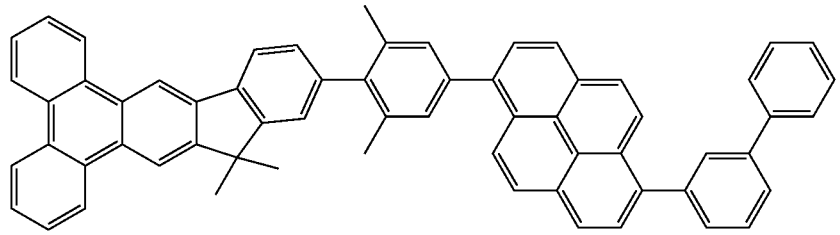

A-15
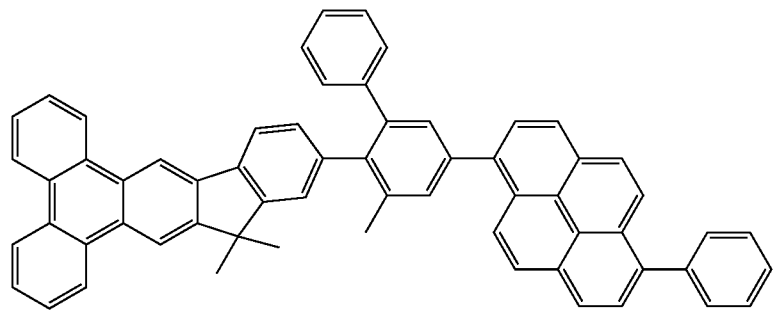
A-16
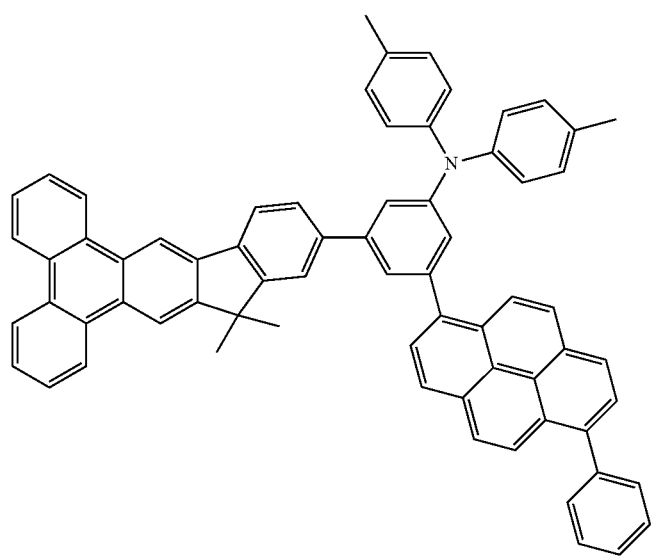
A-17
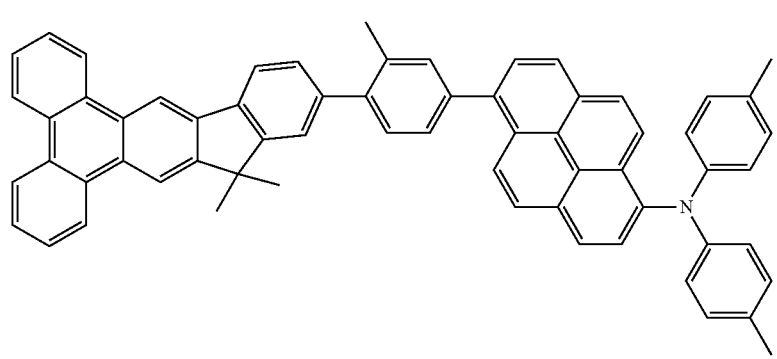

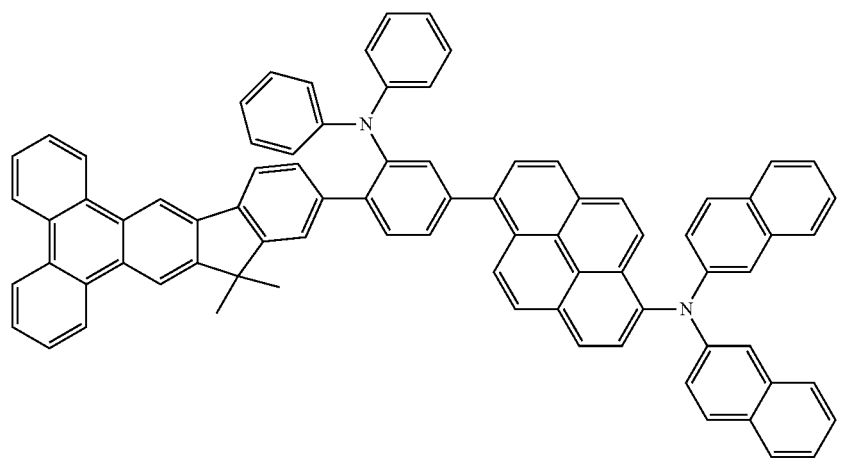
A-18
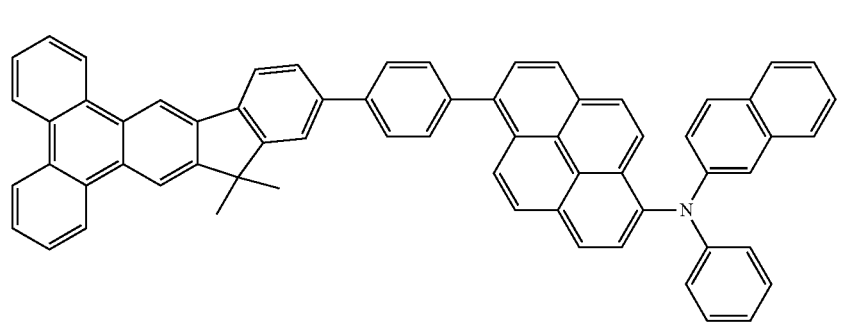
A-19
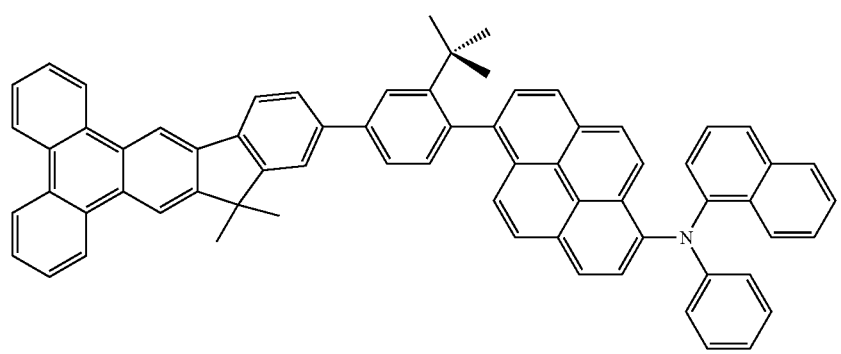
A-20

A-21
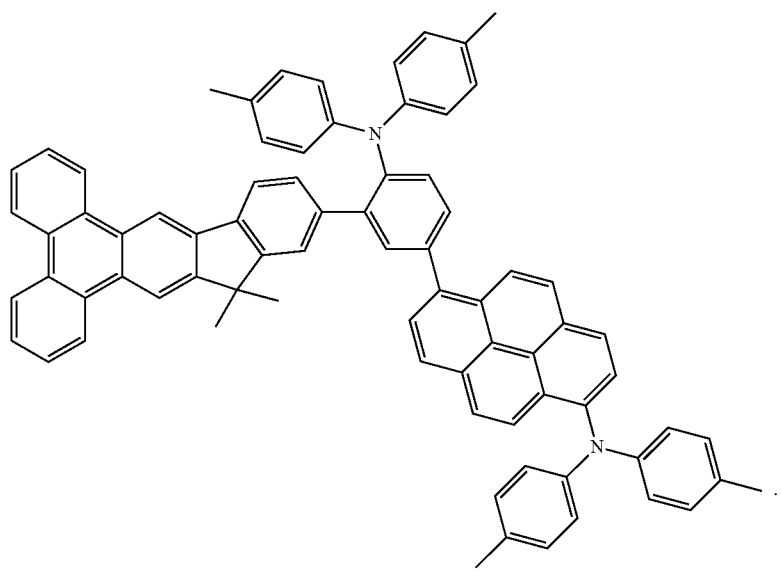
6. According to claim 5, wherein the material functions as a fluorescent emitting layer of organic EL device.
7. According to claim 6, wherein the material functions as a fluorescent blue emitting host or dopant of organic EL device.
* * * * *